United States Patent [19]

Vass

[11] Patent Number: 5,162,232

[45] Date of Patent: Nov. 10, 1992

[54] METHOD FOR DETERMINING THE TIME PERIOD SINCE DEATH OF A HUMAN CADAVER

[75] Inventor: Arpad A. Vass, Oak Ridge, Tenn.

[73] Assignee: The University of Tennessee Research Corporation, Knoxville, Tenn.

[21] Appl. No.: 806,766

[22] Filed: Dec. 13, 1991

[51] Int. Cl.$^5$ ............................................. G01N 33/92
[52] U.S. Cl. ..................................... 436/71; 436/182; 436/183
[58] Field of Search ....................... 436/71, 182, 183; 73/19.09

[56] References Cited

PUBLICATIONS

Rodriguez, W. C. and Bass, W. M., "Insect Activity and its Relationship to Decay Rates of Human Cadavers in East Tennessee," *Journal of Forensic Sciences*, JFSCA vol. 28, No. 2, Apr. 1983, pp. 423–432.

Willey, P. and Heilman, A., "Estimating Time Since Death Using Plant Roots and Stems," *Journal of Forensic Sciences*, JFSCA vol. 32, No. 5, Sep. 1987, pp. 1264–1270.

Perry, W. L., III, Bass, W. M. Riggsby, W. S., and Sirotkin, K., "The Autodegradation of Deoxyribonucleic Acid (DNA) in Human Rib Bone and Its Relationship to the Time Interval Since Death," *Journal of Forensic Sciences*, JFSCA vol. 33, No. 1, Jan. 1988, pp. 144–153.

Haglund, W. D., Reay, D. T., and Swindler, D. R., "Canid Scavenging/Disarticulation Sequence of Human Remains in the Pacific Northwest," *Journal of Forensic Sciences*, JFSCA vol. 34, No. 3, May, 1989, pp. 587–606.

Galloway, A., Birkby, W. H., Jones, A. M., Henry, T. E., and Parks, B. O., "Decay Rates of Human Remains in an Arid Environment," *Journal of Forensic Sciences*, vol. 34, No. 3, May 1989, pp. 607–616.

*Primary Examiner*—James C. Housel
*Assistant Examiner*—Lyle A. Alexander
*Attorney, Agent, or Firm*—Luedeka, Hodges, Neely & Graham

[57] ABSTRACT

A method for determining the time period since the death of a human cadaver deposited on soil by the steps of removing a sample of soil from beneath the cadaver, testing the sample for a concentration of a chemical which is indicative of the time since the death of the human cadaver, and correlating the concentration with the number of accumulated degree days (ADD) to determine the length of time since the death of the human cadaver. The chemicals include fatty acids, such as propionic acid, butyric acid, and valeric acid, and inorganic ions, such as ammonium, calcium, magnesium, sodium, chloride, and sulfate.

6 Claims, 2 Drawing Sheets

METHOD FOR DETERMINING THE TIME PERIOD SINCE DEATH OF A HUMAN CADAVER

The present invention relates to methods for obtaining forensic information. More specifically, the present invention relates to methods for determining the time since death of a human cadaver.

The forensic scientist faces many questions when a corpse is discovered. One of the most difficult tasks is the determination of the "time since death" when the corpse is skeletonized or in an advanced stage of decomposition. Previously, forensic scientists have relied heavily on experience and a few, if any, indicators which could provide them with only rough estimates of the time since death. These indicators (if present) are easily overlooked at the crime scene and can include various parameters such as the number of leaf falls covering skeletal remains, the type of insects which were-/are present, the amount of fungal activity present on bones, the fat content of bones, and the bleaching and exfoliation of cortical surfaces.

The usefulness of such indicators often depends upon the climate, season and circumstances of the crime site. In addition, many of the indicators are easily disturbed upon removal of the corpse. Thus, the forensic scientist is left with very little information to work from and estimates of the time since death are often bracketed by large uncertainties.

Current time since death estimates are based on insect activity and decompositional stages. Other estimates based on the decomposition of associated clothing as well as those of plants and decomposition vectors, and the use of plant roots and stems provide additional information to the forensic scientist. In addition, the use of the degradation rate of DNA in human ribs has been explored as an indicator of time since death. Since clothing, insect activity, and plant material may or may not be present, these methods all have limitations and the use of the corpse itself and the scientist's experience are currently the most consistent factor in time since death determinations.

The present inventor has discovered that the decomposition of a human cadaver produces certain chemical compounds which are deposited in the environment surrounding the corpse. The chemical compounds are deposited at concentrations which are dependent upon the time since the deposition of the cadaver at the site. Thus, the time since death may be determined by determining the concentration of certain chemicals residing (in the soil) underneath the cadaver and determining the decompositional state of the cadaver.

The chemicals which are indicative of the time since the deposition of the human cadaver on soil can be volatile fatty acids or inorganic ions. The acids are selected from the group consisting of propionic acid, butyric acid, and valeric acid. The inorganic ions are selected from the group consisting of ammonium, calcium, magnesium, sodium, potassium, chloride, and sulfate.

In the practice of the invention, the soil beneath the cadavers is sampled. Approximately 10 grams of soil are used for the sample although larger amounts of soil may be used. Control samples are taken from an unaffected area as close to the cadaver as possible. Control samples are generally taken above seepage zones. Separate soil samples are collected to determine the amount of moisture present in the soil at the time of the collection.

The control samples and the samples from beneath the cadaver may be preferably processed directly in the field. Alternatively, the samples may be stored for processing in a laboratory remote from the field. If processed in the field, each soil sample is coarse filtered to remove insects and plant material. Multiple samples (at least two) are then weighed to obtain uniformity. Once weighed, the samples are diluted with ultrapure water at a ratio of 2:1 (water:soil) to extract the soil solution (i.e., the liquid phase between soil particles). The samples are then returned to the laboratory on ice for further processing.

Volatile fatty acids are analyzed by any one of a number of analytical techniques suitable for determining concentrations. For example, gas chromatography or HPLC will provide analysis of sufficient accuracy for the purposes of the present invention.

Similarly, the inorganic ions are analyzed by HPLC, affinity chromatography, atomic absorption spectroscopy, or other appropriate means for determining concentrations.

The concentration of the chemical is directly dependent upon the amount of time the cadaver has been in contact with the soil and the weight of the individual prior to death. The concentration of the chemical in question varies with the accumulated degree day (ADD). The ADD is the sum of the average temperature in degrees centigrade for a period of days. For example, 4 days at an average temperature of 25° C. would give an ADD of 100. Thus, an ADD of 100 may require only a few days in the Summer while requiring several weeks during the Winter.

Volatile fatty acids are primarily breakdown products of both muscle and fat which every human possesses in various concentrations. Muscle, composed of protein, which in turn is composed of amino acids, readily yields to the formation of VFA's through bacterial action. This process is also temperature dependant. Since decomposition involves both aerobic and anaerobic bacteria, VFA's can be formed by both processes. Butyric acid and propionic acid are formed by anaerobic bacteria, primarily in the gut, which produce, in part, a majority of the gases seen in the bloating stage of decomposition.

The decomposition of a corpse is divided into four stages: Stage 1, fresh; Stage 2, bloating; Stage 3, active decomposition; and Stage 4, dry (mummification or skeletonization).

There is a direct correlation between the decompositional stages and volatile fatty acid (VFA) production. This is due in part to the sequential decomposition of proteins and carbohydrates Very little change in VFA's are associated with Stage 1 of decomposition. Bloating, the result of anaerobic fermentation primarily in the gut, causes skin breakage and leakage of fermentation by-products rich in butyric acids. Active decay causes a surge in aerobic as well as anaerobic bacterial by-products which rapidly disappear by the onset of Stage 4.

It is noted that rainfall does not appear to affect these findings. The soil underneath a corpse is protected from precipitation and heavy, mucoid-like secretions produced from anaerobic fermentation seem to bind the soil together making dilutional factors from rainfall insignificant.

If the individual's identity is known, the actual weight of the individual, divided by 150, can be used as the standard. Weight can, at times, be very difficult to estimate, especially if the corpse is severely decomposed or skeletonized. In these instances a range of 50 lbs. may be too narrow for weight estimations and a range of 100 lbs. or even 150 lbs can be used. The closer one can judge the individual's weight, the narrower the "time since death" range will be.

Weight estimations can also be performed by studying the size of clothing found on the corpse, and the robustness of the skeletal material can at least indicate the frame size of the individual.

The optimum sampling depth is determined as that depth of soil beneath the cadaver with the highest pH. Intact cores can be returned to the laboratory on ice until this determination is completed. Cores, if collected, should be at least six inches in depth.

Temperature is by far the most important environmental factor affecting decomposition. This parameter not only affects the breakdown of proteins and carbohydrates, but also affects the insects and bacteria in a similar fashion. When the ambient temperature decreases, so does the rate at which the insects consume the corpse, the rate at which the bacteria break down protein into fatty acids and the way the fatty acids themselves are utilized. Fewer insects digesting less body material results in a greater percentage of protein and carbohydrates turning into VFA's by bacterial action and more VFA's ending up in the soil solution.

The temperature supplied by the National Weather Service can be adjusted to compensate for differences near the corpse. This is accomplished by taking maximum and minimum temperature measurements at the site for at least a week. These values are compared to those obtained from the National Weather Service for the same time period. The differences are averaged to obtain an adjustment value. National Weather Service temperatures are corrected prior to establishing the number of days required to attain the ADD value obtained in the VFA procedure. The number of days obtained by this process is the time since death. The range of VFA's will determine the range for the time since death estimation.

If the average temperature drops below 4° C. it becomes much more difficult to estimate the time since death based on a single time point. The presence of long chain fatty acids in addition to increased millimolar (mmol) concentrations of VFA's will indicate to the investigator that the corpse has been exposed to cold temperatures as well as decreased insect and bacterial activity. In this case, a very detailed knowledge of past temperature conditions will be crucial in making any assessment as to the time since death. Because of the increased salt concentrations in the human body, decomposition still occurs when the temperature falls below 0° C. For this reason any ADD's below 0 degrees are counted as 0 and not as a negative number.

The liberation of VFA's cease at $1285 \pm 110$ Accumulated Degree Days. This also allows one to calculate a decompositional rate. When a corpse is discovered, and soft tissue is still present, the investigator can divide 1285 (the ADD at which complete skeletonization occurs) by the average temperature (C) on the day which the corpse was found and arrive at a maximum time since death. The closer the corpse is to being completely skeletonized, the more likely it is that the estimated maximum time since death approximates the actual time since death. Although crude, the investigator will at least have an idea of the maximum time since death and can begin his investigation at that point The human body contains many different inorganic elements, some of which are found in higher concentrations in specific regions of the body. Electrolytes are the first to leach out of soft tissue and saturate the soil coupling with any available binding sites on soil particles. This happens very rapidly and the remaining ions inundate the soil and are captured in the organic matrix formed from the decomposition of proteins and carbohydrates. Bacteria can utilize a number of these ion complexes in their metabolism, and it quickly becomes apparent that phosphate, bicarbonate and nitrate are rapidly scavenged by the bacteria.

The release of ions from a corpse does not follow the typical stage sequence usually associated with decomposition. There is a large release of elements very rapidly, followed by an equally rapid decline when soft tissue is completely decomposed by 1285 Accumulated Degree Days. The rise of anions and cations after 2250 Accumulated Degree Days is believed to have its origin in the death of large populations of bacteria leaving behind their constituents as well as bone leaching into the soil. Both calcium and magnesium are found in higher concentrations after the 2250 ADD demarcation and indicate bone seepage, although no difference in the bone is visually apparent. With the exception of sulfate, nearly all the anions and cations investigated have almost reached baseline levels after 5250 ADD. Depending on the subjects, this approximates 1.5–2 years worth of decomposition. Sulfate is still present in large amounts after 4 years. Calcium continues to exhibit a cyclic release from skeletal material and is also found in considerable amounts. It is believed that deep cores from underneath the corpse (greater than 2 ft.) could prove useful in determining the time since death of cadavers in advanced skeletal states.

When a skeletonized corpse is found, great care must be taken to note any changes in the bone such as bleaching and exfoliation. Special care must be exercised when dealing with skeletonized or mummified corpses to be sure that close attention is given to ratios between the various ions. This is very important in determining whether or not the corpse has been decomposing greater than 2250 ADD. This may be definitive in terms of pinpointing the time since death of an individual.

This technique is especially valuable when it is noted that rainfall does not appear to affect these findings. The soil underneath a corpse, even if skeletonized, is protected from precipitation for well over a year. The heavy, mucoid-like secretions produced from anaerobic fermentation seem to bind the soil together making dilutional factors from rainfall insignificant.

BRIEF DESCRIPTION OF THE DRAWINGS

In order to provide a better understanding of the present invention, the following examples are given primarily for the purposes of illustrating certain more specific details thereof. The examples may be better understood by reference to the drawings in which.

Figure 1:
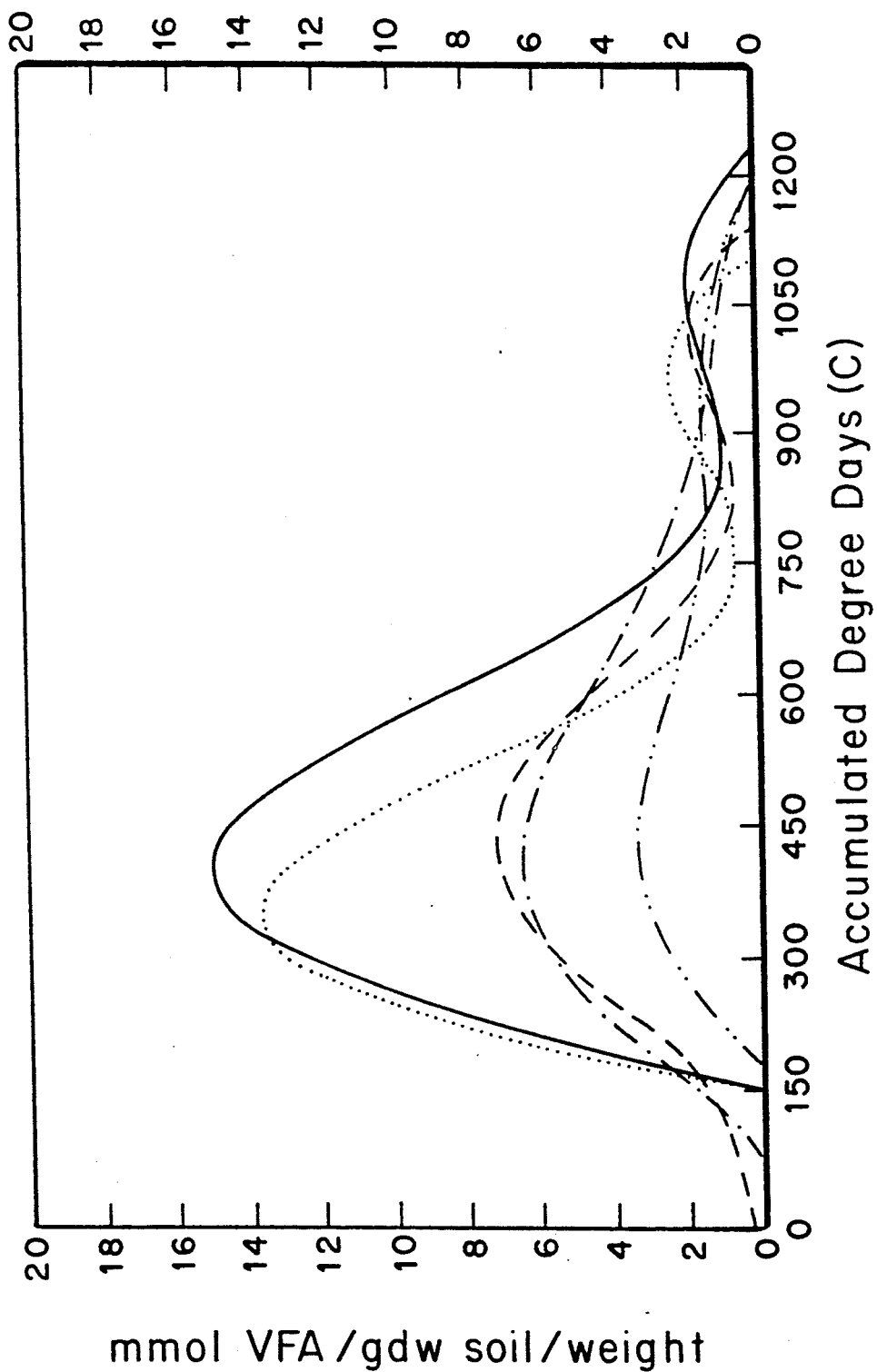
FIG. 1 is a graph of the ratios of volatile fatty acids, over time, in soil solution underneath decomposing corpses.

A total of seven, unembalmed, unautopsied cadavers were placed at a decay research facility at various times of the year (3 in Summer, 1 in Fall, 1 in Fall/Winter, 1 in Winter/Spring, and 1 in Spring). This facility was located in a secluded open-wooded area. The subjects were placed at the research facility within 60 hours of their death. The subjects were stored in morgue coolers prior to the beginning of the decay study. All articles of clothing were removed from the subjects and they were placed face down, arms positioned to the side. The soil was unprepared to simulate natural conditions. Leaves and rocks were removed from underneath the bodies only to allow ease of sampling. The subjects were not protected from the environment in any way. Carnivores were, however, restricted from the site by a chain-linked fence.

Data concerning climatic conditions, body decomposition and insect activity were recorded each sampling period. Data concerning the decay of each cadaver were also recorded.

During the Spring and Summer months, the soil underneath the subjects was sampled every three days. Once the corpses became skeletonized, soil samples were taken weekly. The soil was sampled weekly during the Fall and Winter due to the slower decay rate during the colder months.

Soil sampling was restricted so as to encompass only the region from the pelvis to the shoulders. Sampling was not performed under the arms and legs. The area under each corpse was calculated and mathematically divided into equal areas so that at a depth of 3-5 cm, each area yielded 10 grams of soil. Soil from three randomly selected areas was collected at each sampling period and standard deviation calculations were undertaken to analyze the data.

In order to obtain these samples, the corpses had to be tilted sideways for a brief time. A flat spatula and a soil corer were used to obtain the samples. As soon as the samples were removed, the subjects were placed back on the soil in their original positions. Soil controls were taken during each sampling session from unaffected areas as close to the subjects as possible. Control samples were generally taken above seepage zones and the pH was measured to be sure that they were not contaminated by insect migrations or by permeation.

Separate soil samples were collected to determine the amount of moisture present in the soil at the time of collection. The sample was weighed and placed in a preweighed glass scintillation vial (Baxter), frozen and then lyophilized (Labconco, Kansas City, Mo.) for 24 hours. After the water was completely removed, the vial was again weighed using a balance (Sartorius, Model PT600), and the dry weight recorded.

All samples were processed directly in the field. Each soil sample was filtered through a #8 stainless steel sieve (Baxter, Stone Mountain, Ga.) to remove insects and plant material. This material was weighed using a battery operated balance (Sartorius, Baxter), to obtain uniformity. Once weighed, the samples were placed in 50 ml polypropylene centrifuge tubes (Baxter) and nanopure, deionized water ($>18$ mohm) was added in a ration of 2:1 (water:soil) to extract the soil solution. The samples were then returned to the laboratory on ice for further processing.

All samples were vortexed for 1 minute before centrifugation at $10,000 \times g$ for 40 minutes using an Ultracentrifuge (Sorvall RC2-B, Newport, Conn.). After centrifugation the samples were filtered through a 0.2 $\mu$m low protein binding filter (Acrodisc, Gelman Sciences, Inc.) to remove all microorganisms. These samples were then frozen at $-50°$ C. for later analysis.

EXAMPLE I

Analysis of Volatile Fatty Acids (VFA)

A 500 $\mu$l aliquot of filtered sample was vortexed for 15 seconds and measured for pH (American H3701-3 with a gel-filled epoxy body combination pH probe, Baxter). Volatile fatty acids were analyzed by adding 0.2 $\mu$l formic acid to 0.2 $\mu$l of sample and injecting each sample on a 9A gas chromatograph equipped with a flame ionization detector (FID) (Shimadzu 9A). The carrier gas was nitrogen. The packed column consisted of Chromosorb-W and was maintained at 120° C. The injector temperature was 160° C. Peak heights were analyzed using a Nelson 3000 Series GC interface, Model 2600 (Nelson Analytical, Inc.). VFA standards were purchased from Supelco, Inc. (Bellefonte, Pa.).

Statistical analyses of the data (using the SAS statistical package) included analysis of variance and analysis of covariance with multiple comparisons to test for significant differences.

Two variables were important determinants of the concentration of volatile fatty acids in soil solution: the amount of moisture already present in the soil and the weight of the body prior to decomposition. The effect of moisture was minimized by determining the gram dry weight (gdw) of the soil rather than by using wet weights.

The second variable, pre-death weight, was standardized through the use of a weight correction, since every individual has a different ratio of fat and muscle tissue, which would produce different concentrations of VFA's. This standard is based on the average adult weighing 150 lbs. and was calculated to allow for varying levels of precision in the use of this factor. See Table

TABLE 1

| Weight Standards Based on Increments of 50, 100, and 150 lbs. | | |
| --- | --- | --- |
| | Increments (lbs) | Standard |
| 50 | 0–49 | 0.1667 |
| | 50–99 | 0.5000 |
| | 100–149 | 0.8333 |
| | 150–199 | 1.1677 |
| | 200–249 | 1.5000 |
| | 250–300 | 1.833 |
| 100 | 0–99 | 0.333 |
| | 100–199 | 1.0000 |
| | 200–299 | 1.6667 |
| 150 | 0–149 | 0.5000 |
| | 150–299 | 1.5000 |

FIG. 1 shows the averaged volatile fatty acid data for all seven subjects in millimolar concentrations of VFA's. Once moisture and an individual's weight are taken into account, the VFA concentrations, regardless of the subject, season or year in which the subject began to decompose, are the same for any given total of Accumulated Degree Days (ADD). Control values for the volatile fatty acids examined in this study were insignificant and never exceeded 0.2 mmol/gdw soil.

Therefore, it is possible to estimate the time since death for the individual, given these specific VFA ratios, a gross description of the corpse and National Weather Service data concerning the environmental temperature where the corpse was found.

The ratios of VFA's hold true for any season and any amount of precipitation studied. Areas subjected to constant flooding or extreme moisture may require sampling from greater depths or may be unusable. This procedure could also be unreliable for estimating time since death intervals when dealing with mummified remains.

Decompositional rates were based on the number of Accumulated Degree Days required for VFA production to fall below detectable limits. This coincided with either complete skeletonization or mummification of any remaining soft tissue.

EXAMPLE II

Analysis of Inorganic Ions

All samples were obtained and processed as previously described in Example I. Each soil sample was filtered through a #8 stainless steel sieve (Baxter, Stone Mountain, Ga.) to remove insects and plant material. This material was weighed using a battery operated balance (Sartorius, Baxter), to obtain uniformity. Once weighed, the samples were placed in 50 ml polypropylene centrifuge tubes (Baxter) and nanopure, deionized water (>18 mohm) was added in a ratio of 2:1 (water:-soil) to extract the soil solution. The samples were then returned to the laboratory on ice for further processing.

All samples were vortexed for 1 minute before centrifugation at 10,000 × g for 40 minutes using an ultracentrifuge (Sorvall RC2-B, Newport, Conn.). After centrifugation the samples were filtered through a 0.2 μm low protein binding filter (Acrodisc, German Sciences, Inc.) to remove all microorganisms. These samples were then frozen at −50° C. for later analysis.

A 500 μl aliquot of filtered sample was vortexed for 15 seconds and measured for pH (American H3701-3 with a gel-filled epoxy body combination pH probe, Baxter).

Anions (chloride and sulfate) were analyzed on a conductivity detector (Waters 431) equipped with an autosampler, (Waters WISP 710B) a HPLC pump with noise suppression (Waters Model 510) and an anion column with an anion guard column (Waters Anion IC-Pak A, Milford, Miss.). Cations (ammonium, potassium, calcium, magnesium, and sodium) were analyzed similarly, but utilized a cation column with a cation guard column (Waters Cation IC-Pak C).

Filtered soil solution was placed through a preparatory cartridge (Hamilton Chromatography C18) and 200 μl was placed in the autosampler. To prepare one liter of eluent for anion analysis, 20 ml of buffer concentrate, (851.5 ml distilled deionized water, 23.5 ml gluconic acid solution (50% wt/wt), 8.6 g lithium hydroxide, 34.0 g boric acid, 250.0 ml glycerin) is added to 20 ml n-butanol, 120 ml acetonitrile and 840 ml distilled deionized water. This eluent was then filtered (Magna, Nylon 66 filter, Micronsep, Honeoye Falls, N.Y.). 50 μl of sample was injected with a flow rate of 1.2 ml/min. Peak heights and areas were measured using a Nelson 3000 Series GC interface, Model 2600 (Nelson Analytical, Inc.). Anion standards were made in the laboratory.

Monovalent cations (ammonium, potassium and sodium) required an eluent composed of 2 mM HNO3 and 0.05 mM EDTA per liter of distilled, deionized (>18 mohm) water. Divalent cations (calcium and magnesium) required an eluent composed of 35 μl anhydrous ethylenediamine (EDA) per liter of distilled, deionized (>18 mohm) water, adjusted to pH 5.8–6.2 with nitric acid and/or 0.1 sodium hydroxide. All cation eluents were degassed and filtered with a 0.2 μm mem Membrane Discs, Alltech Associates, Inc., Deerfield, Ill.). 50 μl of sample was injected at a flow rate of 1.2 ml/min. Peak heights and areas were measured using a Nelson 3000 Series GC interface, Model 2600, (Nelson Analytical, Inc.). Cation standards were made in the laboratory.

Statistical analyses of the data (using the SAS statistical package) included analysis of variance and analysis of covariance with multiple comparisons to test the significant differences.

Separate soil samples were collected to determine the amount of moisture present in the soil at the time of collection. The sample was weighed and placed in a preweighed glass scintillation vial (Baxter), frozen and then lyophilized (Labconco, Kansas City, Mo.) for 24 hours. After the water was completely removed, the vial was again weighed using a balance (Sartorius, Model PT600), and the dry weight recorded.

The effects of the amount of moisture in the soil and the weight of the body prior to death were compensated for as in Example I.

The effect of moisture was minimized by determining the gram dry weight (gdw) of the soil rather than by using wet weights.

The second variable, pre-death weight, was standardized through the use of a weight correction, see Table 1, since every individual has a different ratio of fat and muscle tissue producing different concentrations of ions. This standard is based on the average adult weighing 150 lbs. and was calculated to allow for varying levels of precision in the use of this factor.

Figure 2:
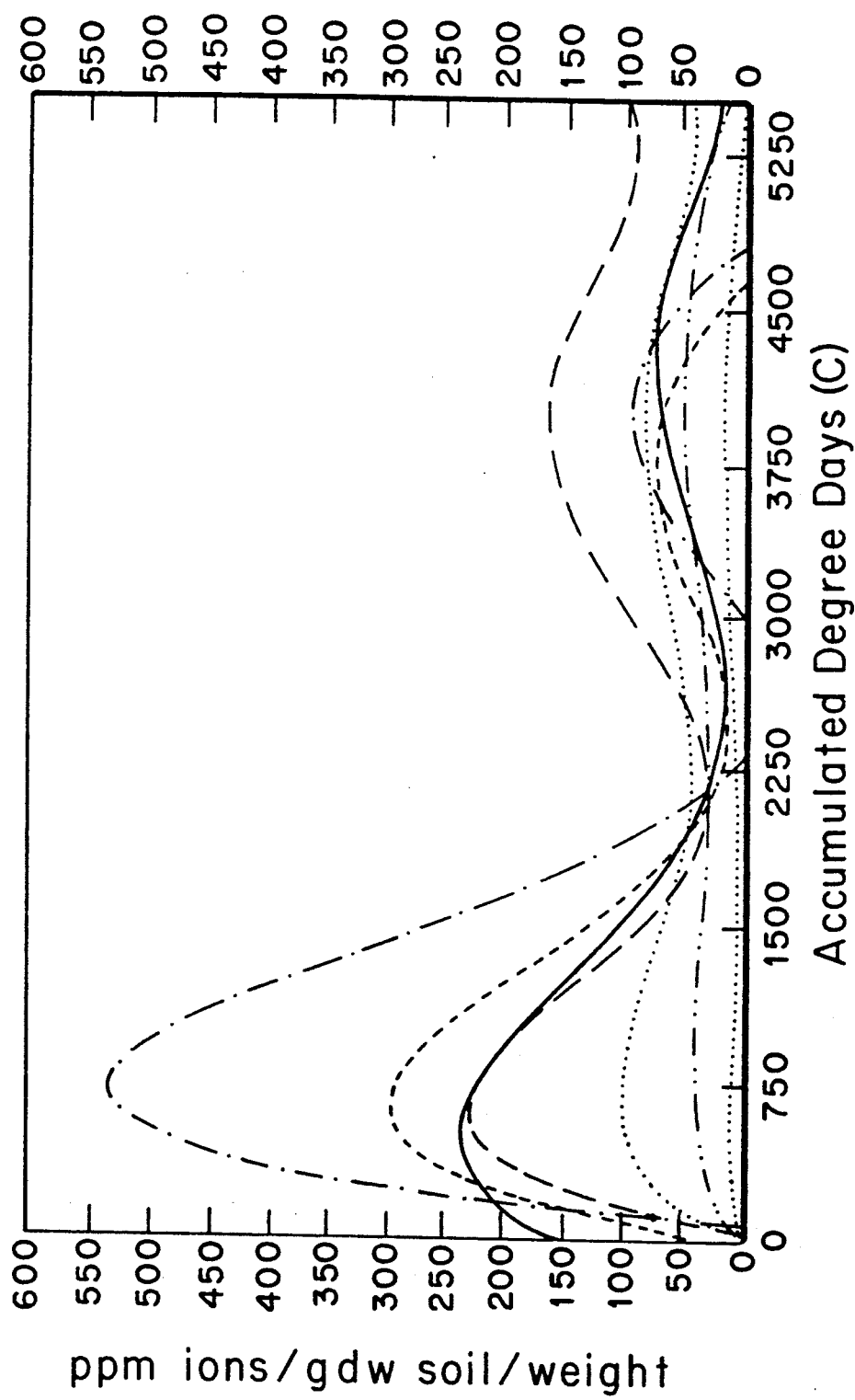
FIG. 2 is a graph of the ratios of anions and cations, over time, in soil solution underneath decomposing corpses.

FIG. 2 shows the relevant anion/cation data for all seven subjects. Once moisture and an indivdual's weight are taken into account, the anion/cation concentrations in parts per million (ppm), regardless of the subject, season or year in which the subject began to decompose, are the same for any given total of Accumulated Degree Days (ADD). Control values for the relevant ions examined in this Example never exceeded 22.0 ppm/gdw soil.

The ratios of ions hold true for any season and any amount of precipitation yet studied. Areas subjected to constant flooding or extreme moisture may require sampling from greater depths or may be unusable.

EXAMPLE III

Calculation Time Since Death Using VFAs

The corpse of a male was found lying in a field. The average temperature for the day was 18° C. Visual inspection of the corpse indicated that he was in late Stage 3 (Active decay) of decomposition. Maggot migrations had apparently already taken place. All indications pointed to the fact that he had decomposed where he was found and had not been moved. Soil samples to a depth of 8 inches were taken from under the corpse with 3 in. diameter aluminum tubes. The ends of the tubes were covered with aluminum foil, labeled as to which side was up, and placed in an ice chest making sure that they stayed dry. Once in the laboratory the cores were opened and using pH paper the most basic region of the core was located. This region (6–8 cm in depth) was then isolated and 10–20 grams was used for VFA determinations.

Using a 2:1 (water:soil) extract yielded 0.58 mmol of n-valeric acid, 0.31 mmol of iso-butyric acid, 1.54 mmol of propionic acid, 0.92 mmol of iso-valeric and 0.3 mmol of n-butyric acid. These concentrations were then adjusted to accommodate any dilutions, soil moisture and the weight of the corpse which, based on skeletal robustness, was estimated to be between 100 and 150 lbs.

Computation for n-butyric acid:

Weight standard (Table 1) : 0.8333
Gram dry weight of 10 grams of soil : 7.38 grams
Dilutional Factors : 20 milliliters of water added to 10 grams of soil $$[((0.3 \times 20)/7.38)/0.8333] = 0.98 \text{ mmol}$$
n-butyric/gdw/weight std.

0.98 correlates to approximately 700 Accumulated Degree Days (FIG. 1). This was performed for each VFA with a resulting ADD range of 675-775. See Table 2. Since propionic acid was still high, any ADD's greater than 800 could be ruled out. Determining the number of days required to obtain 675-775 ADD's resulted in a time since death estimate of 41-48 days. Maximum time since death (MTSD) estimates predicted the MTSD to be 1285/18 = 71 days.

Although the exact time since death is not yet known, the individual in question was subsequently identified and seen alive 52 days prior to finding his corpse.

TABLE 2

| VFA | mmol in Sample | mmol, adjusted | ADD, From FIG. 1 |
|---|---|---|---|
| n-butyric | 0.3 | 0.98 | 700 |
| iso-butyric | 0.31 | 1.01 | 775 |
| n-valeric | 0.58 | 1.89 | 675 |
| iso-valeric | 0.92 | 2.99 | 725 |
| n-propionic | 1.54 | 5.01 | 675 |

EXAMPLE IV

Calculating Time Since Death Using Inorganic Ions

The corpse of a skeletonized young adult was found lying in a ditch. Visual inspection of the corpse indicated that he was in Stage 4 (Dry) of decomposition. All indications pointed to the fact that he had decomposed where he was found and had not been moved. His right leg had been dragged off by a carnivore. Soil samples to a depth of 12 inches were taken from under the corpse with a soil corer. Once in the laboratory the cores were opened and using pH paper the most basic region of the core was located. This region (11-12.5 cm in depth) was then isolated and 10-20 grams was used for anion/cation determinations.

Using a 2:1 (water:soil) extract yielded 27.9 ppm of sulfate, 1.4 ppm chloride, 10.2 ppm sodium, 6.9 ppm potassium, 7.1 ppm calcium. Ammonium and magnesium were below detectable limits. These concentrations were then adjusted to accommodate any dilutions, soil moisture and the pre-death weight of the corpse which, based on his weight at the time of his disappearance, was 96 lbs.

Computation for Sulfate

Weight standard : 96 lbs./150 lbs. = 0.64
Gram dry weigh of 10 grams of soil : 8.64 grams
Dilutional Factors : 20 milliliters of water added to 10 grams of soil $$[((27.9 \times 20)/8.64)/0.64] = 101 \text{ ppm}$$
sulfate/gdw/weight std.

101 correlates to approximately 3000 Accumulated Degree Days (FIG. 2). This was performed for each ion with a resulting ADD range of 2250-3000. See Table 3. Since all other ions were low, any ADD's less than 2000 or greater than 3750 could be ruled out. Lack of appreciable amounts of magnesium present ruled out ADD's greater than 3000. Determining the number of days required to obtain 2250-3000 ADD's resulted in a time since death estimate of 168-183 days. This time frame was within two weeks of when the individual was reported missing, once the victim had been identified.

TABLE 3

| Ion | mmol in Sample | mmol. Adjusted | ADD, From FIG. 2 |
|---|---|---|---|
| sulfate | 27.9 | 101 | 3000 |
| chloride | 1.4 | 5.06 | 2625 |
| sodium | 10.2 | 36.9 | 2250 |
| potassium | 6.9 | 25.0 | 2875 |
| calcium | 7.1 | 25.7 | 2250 |

Thus, the present invention provides a method for determining the time since the deposition of a human cadaver in soil. The method uses the concentration of volatile fatty acids and inorganic ions for this determination.

Various embodiments of the features of the invention which are believed to be new are set forth in the appended claims.

What is claimed is:

1. A method for determining the time period since death of a human cadaver deposited on soil, the method comprising:

removing a sample of soil from beneath torso of the cadaver;

testing the sample by gas chromatography, high pressure liquid chromatography, affinity chromatography or atomic absorption spectroscopy for the presence and concentration of chemicals comprising volatile fatty acids and inorganic ions which are indicative of the time since death of the human cadaver; and correlating the concentration with the number of Accumulated Degree Days since the death of the human cadaver wherein the accumulated degree days is the sum as of the average temperature in degree centigrade for a given period of days.

2. The method of claim 1 wherein the volatile fatty acid is selected from the group consisting of propionic acid, butyric acid, and valeric acid.

3. The method of claim 1 wherein the inorganic ion is selected from the group consisting of ammonium, calcium, potassium, magnesium, sodium, chloride, and sulfate.

4. The method of claim 1 wherein the chemicals is contained in an organic matrix between soil particles.

5. The method of claim 4 wherein the step of testing the sample comprises the steps of:

coarse filtering the sample to remove insect and plant material;

eluting the sample with water to extract the liquid phase between soil particles; and analyzing the water extract for the presence and concentration of the chemicals which is indicative of the time since death of the human cadaver.

6. The method of claim 1 wherein the step of correlating the concentration comprises the steps of:

estimating the weight of the cadaver at the time of death;

diluting the sample with water after removal from beneath the cadaver;

removing a second sample of soil adjacent to said cadaver and determining the moisture content of the second soil sample;

correcting the number of accumulated degree days since death using said estimated weight, said dilution of water and the moisture content of the second soil sample.

* * * * *